(12) United States Patent
Lu

(10) Patent No.: US 9,500,378 B2
(45) Date of Patent: Nov. 22, 2016

(54) ELECTRIC FIREPLACE HAVING HUMIDIFYING DEVICE

(71) Applicant: DONG GUAN SONG WEI ELECTRIC TECHNOLOGY CO., LTD, Dongguan (CN)

(72) Inventor: Weilin Lu, Dongguan (CN)

(73) Assignee: DONG GUAN SONG WEI ELECTRIC TECHNOLOGY CO., LTD, Dongguan, Guangdong (CN)

( * ) Notice: Subject to any disclaimer, the term of this patent is extended or adjusted under 35 U.S.C. 154(b) by 221 days.

(21) Appl. No.: 14/569,606

(22) Filed: Dec. 12, 2014

(65) Prior Publication Data

US 2016/0169537 A1    Jun. 16, 2016

(51) Int. Cl.
| | | |
|---|---|---|
| A61L 9/00 | (2006.01) | |
| F25D 17/06 | (2006.01) | |
| B67D 1/07 | (2006.01) | |
| B01D 47/00 | (2006.01) | |
| B65B 3/00 | (2006.01) | |
| F24D 13/00 | (2006.01) | |
| F24F 6/02 | (2006.01) | |
| A61L 9/12 | (2006.01) | |

(52) U.S. Cl.
CPC .............. *F24D 13/00* (2013.01); *A61L 9/12* (2013.01); *F24F 6/025* (2013.01)

(58) Field of Classification Search
CPC ............ B05B 17/00; F24F 6/00; F24F 3/16; B60H 1/3202; B60H 1/3233
USPC ................. 422/305–306; 62/93, 285, 298; 222/192, 562; 261/66, 72.1, 104, 107; 220/86.1
See application file for complete search history.

(56) References Cited

U.S. PATENT DOCUMENTS

| | | | | |
|---|---|---|---|---|
| 4,049,196 A | * | 9/1977 | Bergami, Jr. | ......... F24C 15/003 126/113 |
| 6,328,220 B1 | * | 12/2001 | Taylor | .................. F24C 15/003 237/78 R |

FOREIGN PATENT DOCUMENTS

CN          203560983 U    *   4/2014    .............. F21S 10/02

OTHER PUBLICATIONS

European Patent Office English Translation of CN 203560983 U.*

* cited by examiner

*Primary Examiner* — Monzer R Chorbaji

(57) ABSTRACT

The present invention discloses an electric fireplace having a humidifying device. The electric fireplace includes a casing. A flame imitation device, a heating device, an air purifying device, the humidifying device, and a touch control panel are provided in the casing. The electric fireplace is combined with the flame imitation device, the air purifying device, and the heating device to provide multiple functions. The user can watch the realistic flame and inhale fresh but not dry warm wind. The humidifying device includes a water container, a cotton rod, a fixing knob, an atomization plate, a hollow pipe, and a fog output box. The humidifying device delivers the water to the atomization plate through the cotton rod to generate atomized particles. The present invention has a simple structure and can be produced easily.

10 Claims, 8 Drawing Sheets

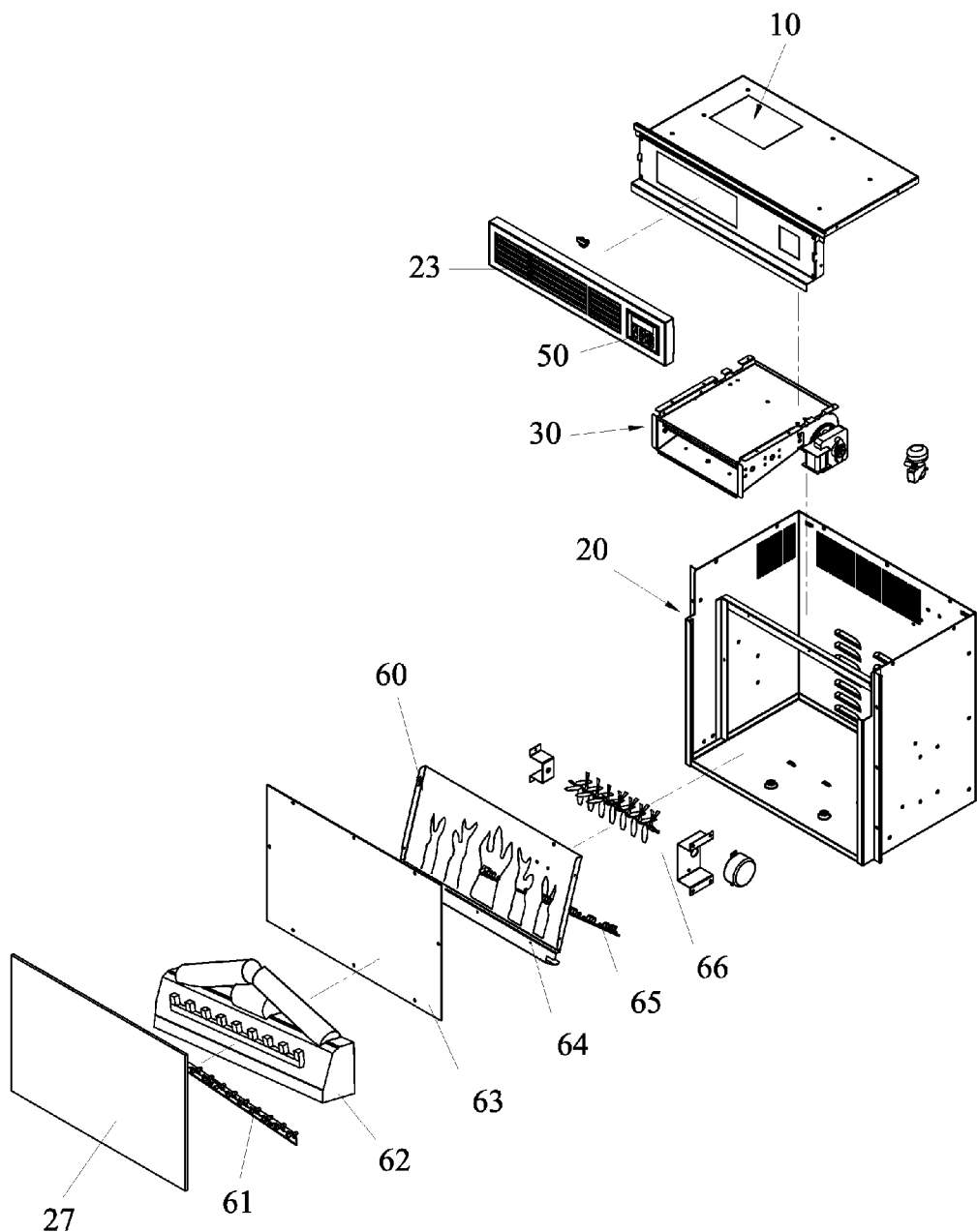
F I G. 4

ELECTRIC FIREPLACE HAVING HUMIDIFYING DEVICE

BACKGROUND OF THE INVENTION

1. Field of the Invention

The present invention relates to an electric fireplace, and more particularly to an electric fireplace having a humidifying device.

2. Description of the Prior Art

A conventional electric fireplace, as disclosed in CN1635305A, comprises a casing. The casing is provided with an electric heater and a flame imitation mechanism. The flame imitation mechanism comprises an imitation burning bed located at the front of a cavity of the casing, a flame image screen close to the back of the imitation burning bed, a light source at the rear of the casing, and a turning sleeve fitted on the light source. The surface of the turning sleeve is formed with a plurality of flame-shaped holes. The light of the light source inside the flame-shaped holes projects on the flame image screen to form a burning flame pattern. The turning sleeve is connected with a motor through a transmission mechanism.

This conventional electric fireplace has simple functions, watching flame and providing warm air. But, because the current environmental pollution is getting worse, people pay more attention to health. Humidity and air pollution have a very close relationship with people's life. When the humidity is too less, people's skin is dry, rough, and aging. Sometimes, the lips are also dry or the throat is itching, or even it causes a sore throat, wheezing, etc. This is one of the reasons for people to be not acclimatized. If the air is too polluted, people breathe very uncomfortably and it may cause a variety of respiratory diseases. Accordingly, the inventor of the present invention has devoted himself based on his many years of practical experiences to solve this problem.

SUMMARY OF THE INVENTION

The primary objective of the present invention is to provide an electric fireplace having a humidifying device to overcome the shortcomings of the prior art. Through a cotton rod, water is sent to an atomization plate to directly generate atomized particles. The design and structure of the present invention are simple. The electric fireplace is combined with a flame imitation device, an air purifying device, and a heating device to provide multiple functions. The user can watch the realistic flame and inhale fresh but not dry warm wind.

In order to achieve the aforesaid objective, the humidifying device of the electric fireplace comprises a water container, a cotton rod, a fixing knob, an atomization plate, a hollow pipe, and a fog output box. The water container has a water inlet. The cotton rod is inserted into the water container from the water inlet to suck water in the water container and send the water to the atomization plate. The fixing knob is rotatably connected to the water inlet of the water container to fix an upper end of the cotton rod. The atomization plate is disposed on top of the fixing knob and in contact with the cotton rod. The atomization plate generates atomized particles to be sent to the hollow pipe. One end of the hollow pipe is connected to the fixing knob through a connector. Another end of the hollow pipe is connected to the fog output box. The atomized particles generated by the atomization plate pass through the hollow pipe to be exhausted through the fog output box.

The feature of the present invention is that the electric fireplace is combined with the flame imitation device, the air purifying device, and the heating device to provide multiple functions. The user can watch the realistic flame and inhale fresh but not dry warm wind. Besides, the humidifying device delivers the water to the atomization plate through the cotton rod to generate atomized particles. The present invention has a simple structure and can be produced easily.

BRIEF DESCRIPTION OF THE DRAWINGS

FIG. 4 is a second exploded view showing the electric fireplace according to the preferred embodiment of the present invention;

DETAILED DESCRIPTION OF THE PREFERRED EMBODIMENTS

Figure 1:
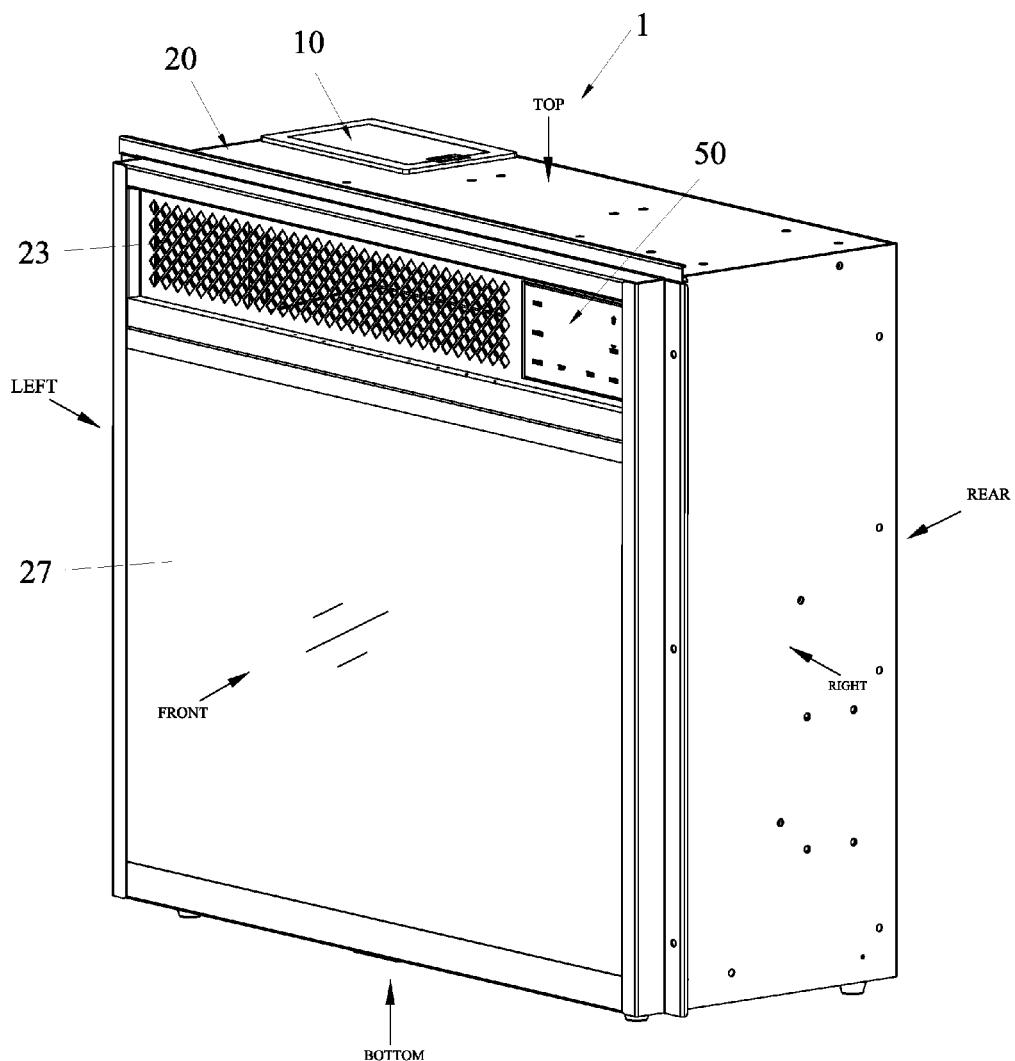
FIG. 1 is a perspective view showing the electric fireplace according to a preferred embodiment of the present invention.

Embodiments of the present invention will now be described, by way of example only, with reference to the accompanying drawings.

As shown in FIG. 1 to FIG. 6, the present invention discloses an electric fireplace 1 having a humidifying device 10. The humidifying device 10 is disposed in the electric fireplace 1 for the electric fireplace 10 to exhaust warm but not dry air. The electric fireplace 1 comprises a humidifying device 10, a casing 20, a heating device 30, an air purifying device 40, a touch control panel 50, and a flame imitation device 60.

Figure 2:
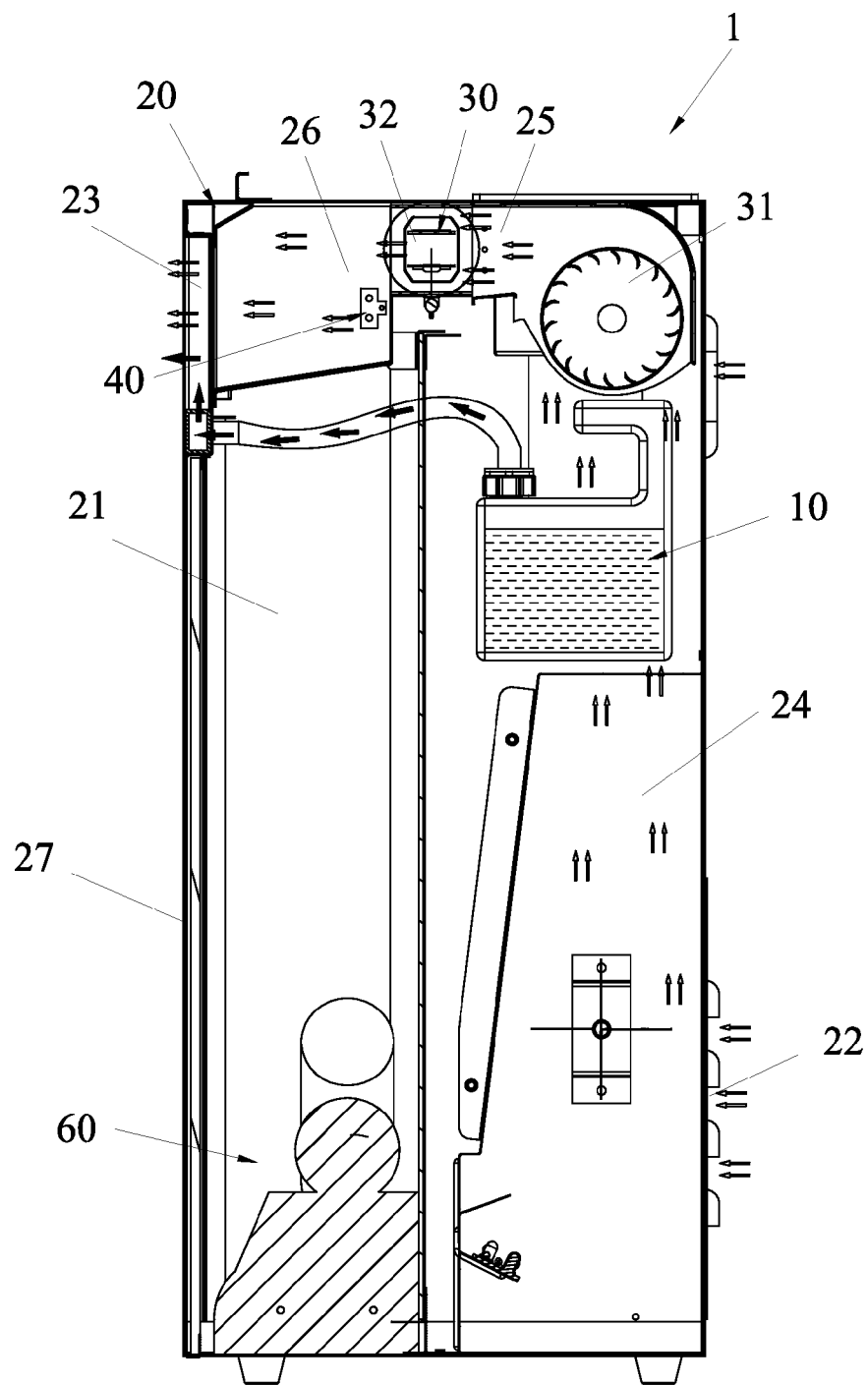
FIG. 2 is a schematic view showing the interior passages of the electric fireplace according to the preferred embodiment of the present invention.
Figure 3:
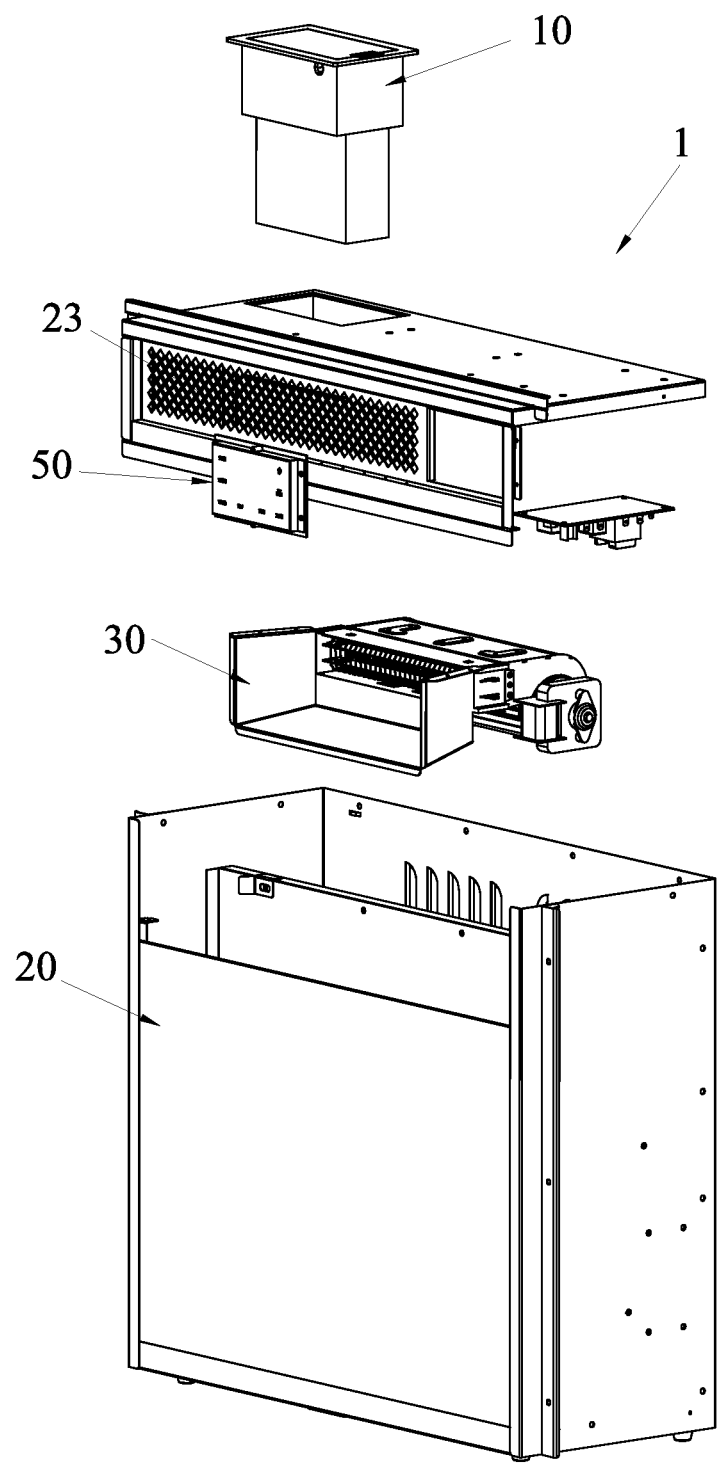
FIG. 3 is a first exploded view showing the electric fireplace according to the preferred embodiment of the present invention.
Figure 5:
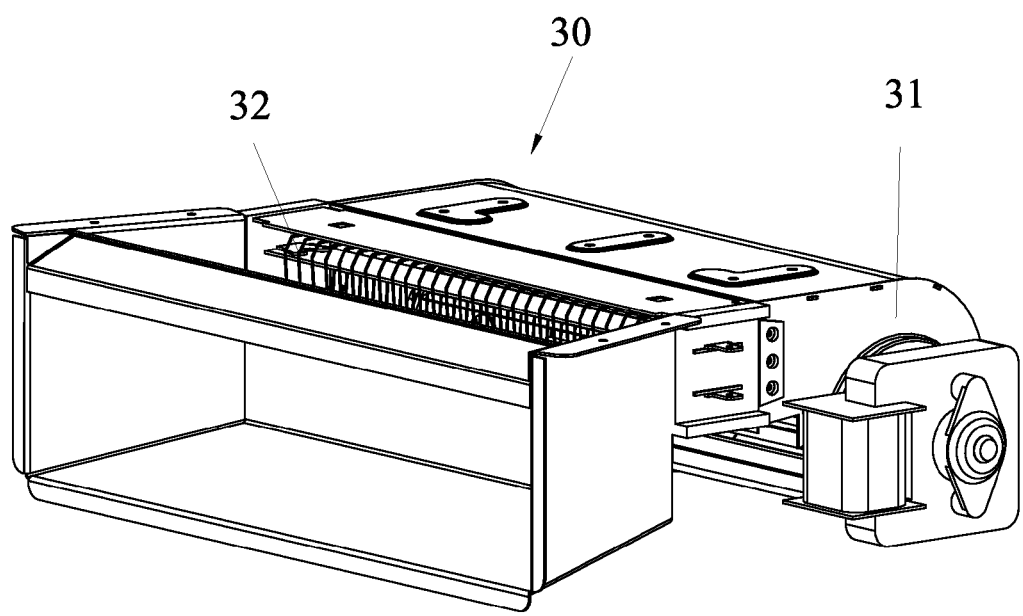
FIG. 5 is a schematic view showing the heating device according to the preferred embodiment of the present invention.
Figure 6:
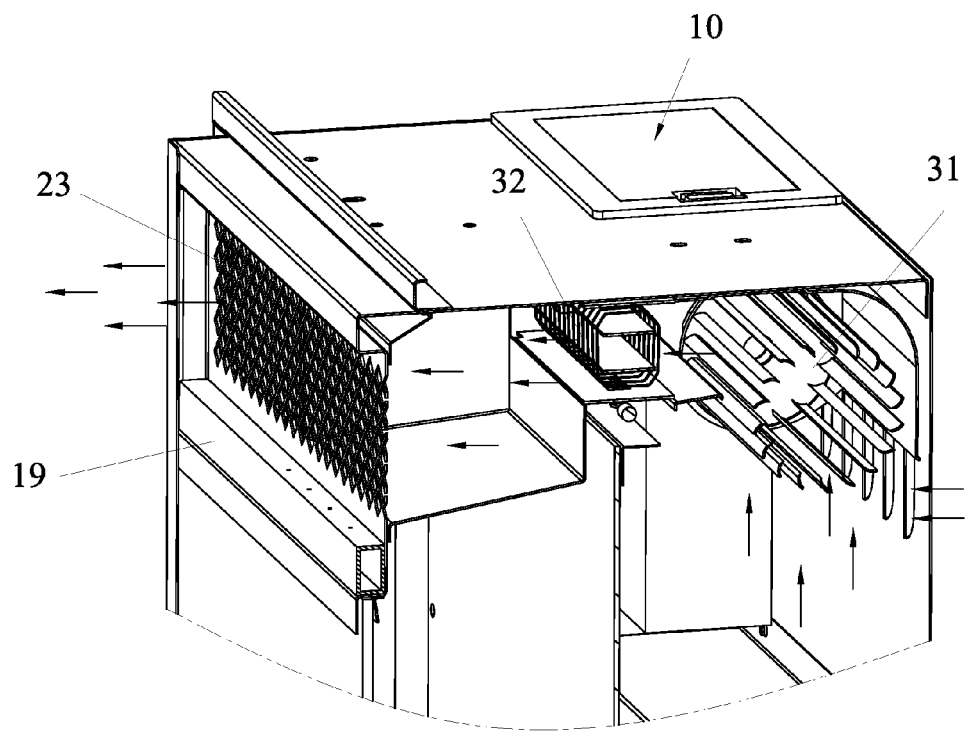
FIG. 6 is a schematic view showing installation of the heating device according to the preferred embodiment of the present invention.

As shown in FIG. 2, the casing 20 has an accommodation room 21 therein. The casing 20 has an air inlet 22 and an air outlet 23 thereon. The air inlet 22 is disposed at a rear side of the casing 20. The air outlet 23 is disposed at a front side of the casing 20. An air inlet passage 24, a heating passage 25, and an air purifying passage 26 are formed in sequence between the air inlet 22 and the air outlet 23. The front side of the casing 20 has a transparent window 27 for watching the imitation flame of the electric fireplace 1. The transparent window 27 is provided with tempered glass. In this embodiment, the air inlet passage 24 is perpendicular to the heating passage 25. The air inlet passage 24 is disposed close to the rear wall of the accommodation room 21. The heating passage 25 is disposed close to the top wall of the accommodation room 21. The heating passage 25 is parallel to the air purifying passage 26. The air purifying passage 26 faces the air outlet 23.

The flame imitation device 60 is mounted at the lower end of the accommodation room 21. The flame imitation device 60 comprises a first light source 61, an imitation charcoal 62, an image screen 63, a flame-shaped plate 64, a second light source 65, and a light reflection assembly 66 which are arranged in sequence inward from the window 27. The tempered glass of the transparent window 27 is to separate the flame imitation device 60 in the casing 20. The imitation charcoal 62 is disposed in front of the image screen 63. The first light source 61 is disposed under the imitation charcoal 62. The first light source 61 is an LED lamp or a low voltage lamp for the imitation charcoal 62 to have a burning effect. A flame image room is defined between the back of the image screen 63 and the back board of the casing 20. The flame image room is provided with a motor to bring the light reflection assembly 66 to rotate. The flame-shaped plate 64 is disposed between the light reflection assembly 66 and the image screen 63. The second light source 65 is disposed under the light reflection assembly 66. When the light reflection assembly 66 is rotated, the light from the second light source 65 is reflected to the flame-shaped plate 64 to form a flame pattern on the image screen 63. The user can watch the realistic flame through the front of the tampered glass.

The heating device 30 is mounted at the upper end of the accommodation room 21. The heating device 30 comprises an exhaust fan 31 and a heating member 32. The exhaust fan 31 has an air suction opening facing the air inlet passage 24 and an air supply opening facing the heating passage 25. The heating member 32 is disposed in the heating passage 25 corresponding to the air supply opening of the exhaust fan 31. In this embodiment, the heating device 30 is provided with a thermo switch for overheating protection. The heating member 32 is a quarta tube heater, a heating coil, or a PTC (positive temperature coefficient) heater. The air suction opening and the air supply opening of the exhaust fan 31 are perpendicular to each other, corresponding to the air inlet passage 24 and the heating passage 25 which are perpendicular to each other. The air suction opening of the exhaust fan 31 faces the air inlet passage 24, and the air supply opening faces the heating passage 25. The exhaust fan 31 is connected between two passages to ensure a strong wind to be blown out.

The air purifying device 40 is installed in the air purifying passage 26 to purify the air flowing through the air purifying passage 26. In this embodiment, the air purifying device 40 is a negative ion generator, a positive ion generator, a positive and negative ion generator, or an ozone generator. Because the air purifying device 40 is directly disposed in the air purifying passage 26, the wind from the heating device 30 flows through the air purifying passage 26 to be purified by the air purifying device 40 to generate negative ions, positive ions, positive and negative ions, or ozone so as to send fresh warm wind out.

Figure 7:
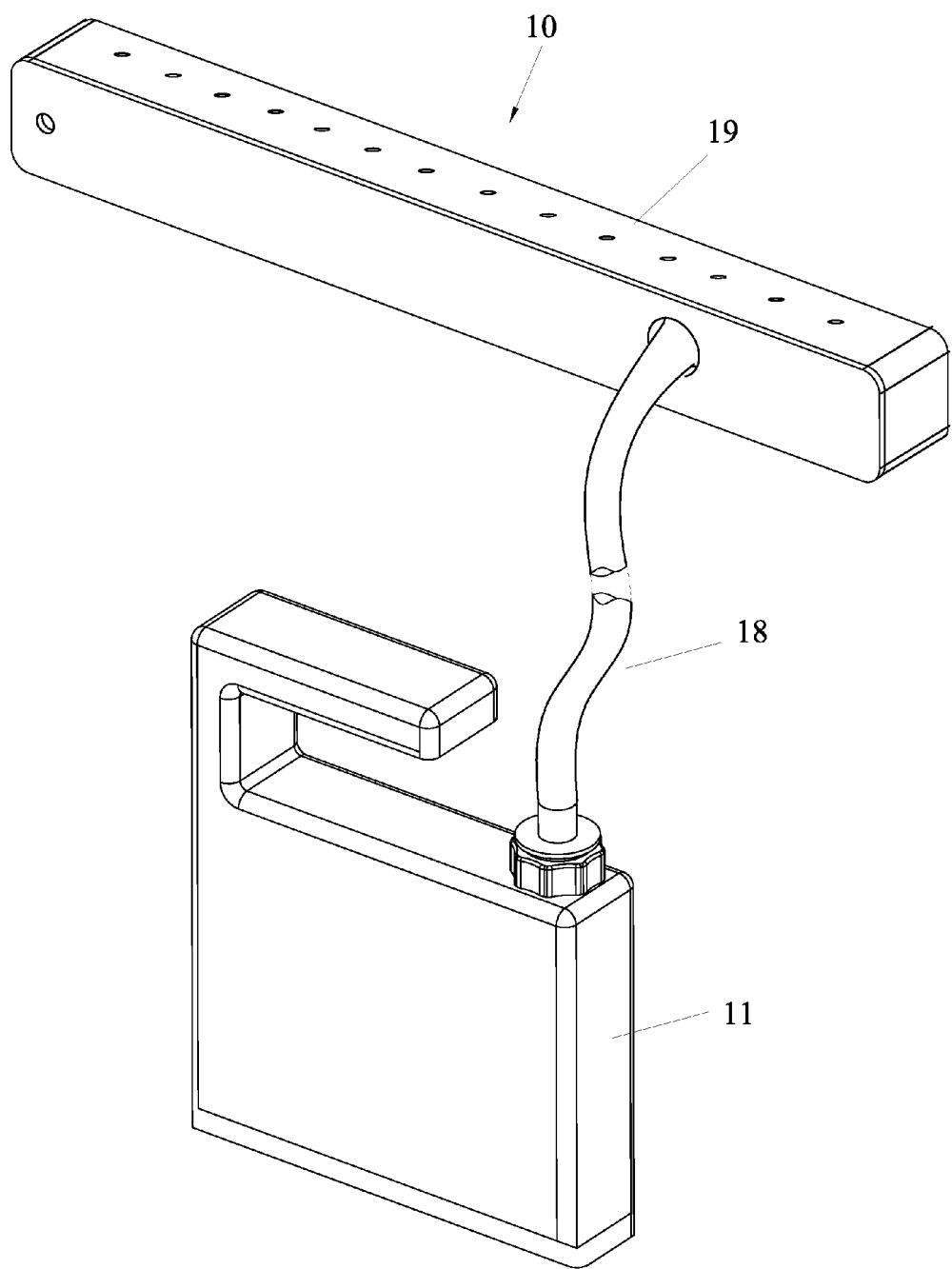
FIG. 7 is a perspective schematic view showing the humidifying device according to the preferred embodiment of the present invention.
Figure 8:
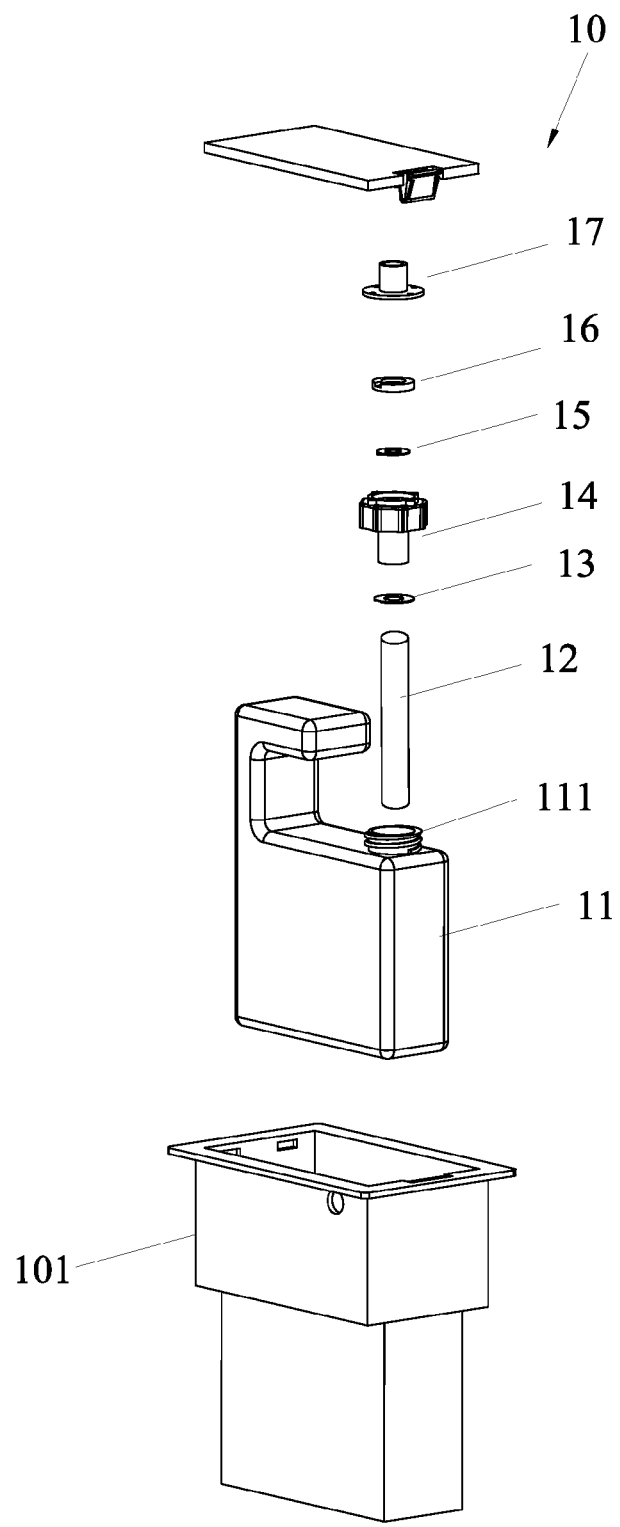
FIG. 8 is an exploded schematic view showing the humidifying device according to the preferred embodiment of the present invention.

As shown in FIG. 7 and FIG. 8, the humidifying device 10 comprises a water container retainer 101, a water container 11, a cotton rod 12, a waterproof ring 13, a fixing knob 14, a seal gasket 15, an atomization plate 16, a connector 17, a hollow pipe 18, and a fog output box 19.

The water container retainer 101 is adapted to drain water and to retain the water container 11. The water container retainer 101 has a barrel and a cover. The water container 11 is placed in the space surrounded by the barrel and the cover. When installed, the water container retainer 101 is placed in a hole formed on the top of the casing 20. It is very convenient for assembly and disassembly. The water container 11 supplies water to the cotton rod 12. The water container 11 has a water inlet 111. The cotton rod 12 is inserted into the water container 11 from the water inlet 111 to suck the water in the water container 11 and send the water to the atomization plate 16. The fixing knob 14 is rotatably connected to the water inlet 111 of the water container 11 to fix the upper end of the cotton rod 12. The waterproof ring 13 is disposed between the fixing knob 14 and the water inlet 111 of the water container 11 to prevent the water container 11 from leaking, providing a sealing function. The atomization plate 16 is disposed on top of the fixing knob 14 and in contact with the cotton rod 12. The atomization plate 16 vibrates to generate atomized particles to be sent to the hollow pipe 18. The seal gasket 15 is disposed between the atomization plate 16 and the fixing knob 14 to prevent leakage after the atomization plate 16 vibrates, providing a sealing and elastic function. One end of the hollow pipe 18 is connected to the fixing knob 14 through the connector 17. The connector 17 is to tighten the atomization plate 16 to prevent it from loosening. Another end of the hollow pipe 18 is connected to the fog output box 19. The atomized particles generated by the atomization plate 16 are sent to the fog output box 19 through the hollow pipe 18 to exhaust humidity.

In the present invention, the atomization plate 16 of the humidifying device 10 is connected with the water inlet 111 of the water container 11 to form an integral one for easy installation. The hollow pipe 18 of the humidifying device 10 can be a soft pipe or a hard pipe for delivering the atomized water to the fog output box 19. The connector 17 between the hollow pipe 18 and the fixing knob 14 can be a fixed connector or a snap-in connector to achieve a quick installation. Furthermore, the fixing knob 14 is provided with a water detection switch. When the water level of the water container 11 is lower than the pre-set value to cause that the cotton rod 12 lacks water, the water detection switch will automatically cut off the power source of the atomization plate 16 to achieve smart monitor and control of the water level.

The humidifying device 10 of the present invention is assembled as the following process. The cotton rod 12 is connected with the water container 11. The atomization plate 16 is secured to on the fixing knob 14. The fixing knob 14 is further connected with the cotton rod 12. The fog output box 19 is connected with the hollow pipe 18. When the humidifying device 10 is assembled to the electric fireplace 1, the water container 11, the cotton rod 12, the fixing knob 14, the atomization plate 16 are installed in the accommodation room 21 of the casing 20. The fog output box 19 of the humidifying device 10 is installed at the front side of the casing 20 and corresponds in position to the air outlet 23. Thus, the air outlet 23 is adapted to exhaust hot wind and purified fresh air. The fog output box 19 of the humidifying device 10 is disposed at the lower end of the air outlet 23. The wind direction of the fog outlet of the fog output box 19 is perpendicular to the wind direction of the air outlet 23 for the humidified and atomized air to be exhausted along with the air of the air outlet 23 to get fresh warm wind, but not dry.

As shown in FIG. 1, the touch control panel 50 is installed at the front side of the casing 20. The touch control panel 50 is electrically connected with the heating device 30, the air purifying device 40, and the humidifying device 10, respectively, for showing the temperature, humidity and light alarm. The touch control panel 50 makes the operation of the electric fireplace 1 more convenient. Through the touch control panel 50, the user can turn on/off the electric fireplace 1 and starts the heating device 30, the air purifying device 40, the humidifying device 10, and the flame imitation device 60 by way of various election modes. Besides, the detection data of the detection switch of each device can be shown on the panel. For example, when the water level of the water container 11 is too low, the water detection switch will automatically cut off the power source of the atomization plate 16. The signal output end of the water detection switch is connected with the signal input end of the touch control panel. The panel will show a light alarm.

The work principle of the electric fireplace 1 is described hereinafter. When the heating device 30 is started, the exhaust fan 31 will inhale the air from the air inlet 22 at the back of the electric fireplace 1 and the air inlet passage 24 to enter the exhaust fan 31. Before entering the exhaust fan 31, the back of the electric fireplace 1 is provided with a filter to filter the dust, preventing inhaled big particles from damaging the exhaust fan 31. The air supply opening of the exhaust fan 31 is directly connected with the heating passage 25. The heating member 32 in the heating passage 25 heats the air to generate warm wind. The warm wind flows to the air purifying passage 26. The air purifying device 40 is disposed in the air purifying passage 26 to generate negative ions, positive ions, positive and negative ions, or ozone for the warm wind to be more fresh. The fresh warm wind is exhausted from the air outlet 23 at the front of the electric fireplace 1. The humidifying device 10 can be synchronously started when the electric fireplace 1 is started, alternatively, it can be manually started according to the demand of the user. After the humidifying device 10 is started, the atomization plate 16 vibrates to atomize the water in the water container 11. The atomized particles are delivered to the fog output box 19 through the hollow pipe 18. The fog outlet of the fog output box 19 corresponds to the air outlet 23, so that the air outlet 23 is to exhaust the warm wind, humidified air and purified air.

The feature of the present invention is that the electric fireplace is combined with the flame imitation device, the air purifying device, and the heating device to provide multiple functions. The user can watch the realistic flame and inhale fresh but not dry warm wind. Besides, the humidifying device delivers the water to the atomization plate through the cotton rod to generate atomized particles. The present invention has a simple structure and can be produced easily.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. An electric fireplace having a humidifying device, the humidifying device comprising a water container, a cotton rod, a fixing knob, an atomization plate, a hollow pipe, and a fog output box; the water container having a water inlet; the cotton rod being inserted into the water container from the water inlet to suck water in the water container and send the water to the atomization plate; the fixing knob being rotatably connected to the water inlet of the water container to fix an upper end of the cotton rod; the atomization plate being disposed on top of the fixing knob and in contact with the cotton rod, the atomization plate generating atomized particles to be sent to the hollow pipe; one end of the hollow pipe being connected to the fixing knob through a connector, another end of the hollow pipe being connected to the fog output box, the atomized particles generated by the atomization plate passing through the hollow pipe to be exhausted through the fog output box.

2. The electric fireplace having a humidifying device as claimed in claim 1, wherein a waterproof ring is provided between the fixing knob and the water inlet of the water container, and a seal gasket is provided between the atomization plate and the fixing knob.

3. The electric fireplace having a humidifying device as claimed in claim 1, wherein the hollow pipe is one of a soft pipe and a hard pipe.

4. The electric fireplace having a humidifying device as claimed in claim 1, wherein the fixing knob is provided with a water detection switch, when the water level of the water container is lower than a pre-set value to result in that the cotton rod lacks water, the water detection switch automatically cuts off a power source of the atomization plate.

5. The electric fireplace having a humidifying device as claimed in claim 1, wherein the connector between the hollow pipe and the fixing knob is one of a fixed connector and a snap-in connector.

6. The electric fireplace having a humidifying device as claimed in claim 1, wherein the electric fireplace comprises:
a casing, the casing having an accommodation room therein, the casing having an air inlet and an air outlet thereon, the air inlet being disposed at a rear side of the casing, the air outlet being disposed at a front side of the casing, an air inlet passage, a heating passage, and an air purifying passage being formed in sequence between the air inlet and the air outlet, the front side of the casing having a transparent window for watching imitation flames of the electric fireplace;
a flame imitation device, the flame imitation device being mounted at a lower end of the accommodation room, the flame imitation device comprising a first light source, an imitation charcoal, an image screen, a flame-shaped plate, a second light source, and a light reflection assembly which are arranged in sequence inward from the window;
a heating device, the heating device being mounted at an upper end of the accommodation room, the heating device comprising an exhaust fan and a heating member, the exhaust fan having an air suction opening facing the air inlet passage and an air supply opening facing the heating passage, the heating member being disposed in the heating passage corresponding to the air supply opening of the exhaust fan;
an air purifying device, the air purifying device being installed in the air purifying passage to purify air flowing through the air purifying passage; and
a touch control panel, the touch control panel being installed at the front side of the casing, the touch control panel being electrically connected with the heating device, the air purifying device, and the humidifying device respectively for showing temperature, humidity and light alarm;
wherein, the water container, the cotton rod, the fixing knob, and the atomization plate of the humidifying device are installed in the accommodation room of the casing, and the fog output box of the humidifying device is installed at the front side of the casing and corresponds in position to the air outlet.

7. The electric fireplace having a humidifying device as claimed in claim 6, wherein the air inlet passage is perpendicular to the heating passage, the air inlet passage is disposed close to a rear wall of the accommodation room, the heating passage is disposed close to a top wall of the accommodation room, the heating passage is parallel to the air purifying passage, and the air purifying passage faces the air outlet.

8. The electric fireplace having a humidifying device as claimed in claim 6, wherein the heating device is provided with a thermo switch for overheating protection.

9. The electric fireplace having a humidifying device as claimed in claim 6, wherein the heating member is one of a quarta tube heater, a heating coil, and a PTC (positive temperature coefficient) heater.

10. The electric fireplace having a humidifying device as claimed in claim 6, wherein the air purifying device is one of a negative ion generator, a positive ion generator, a positive and negative ion generator, and an ozone generator.

\* \* \* \* \*